United States Patent [19]
Whidden

[11] Patent Number: 5,551,089
[45] Date of Patent: Sep. 3, 1996

[54] DESIGNER EARMUFF HAVING INTERCHANGEABLE EAR MUFF PIECES

[76] Inventor: Jenna Whidden, 405 E. 78th St., New York, N.Y. 10021

[21] Appl. No.: 370,677

[22] Filed: Jan. 10, 1995

[51] Int. Cl.[6] ................................... A42B 1/06
[52] U.S. Cl. ............................... 2/209; 128/866
[58] Field of Search .................... 2/208, 209, 423, 2/2; 128/864, 866

[56] References Cited

U.S. PATENT DOCUMENTS

| | | |
|---|---|---|
| 2,924,672 | 2/1960 | Cagen .......................... 2/209 |
| 3,148,376 | 9/1964 | Aileo ........................ 128/866 |
| 3,562,816 | 2/1971 | Hutchinson . | 
| 3,686,691 | 8/1972 | Anderson ..................... 2/209 |
| 4,463,223 | 7/1984 | Yamanoi et al. . |
| 4,471,496 | 9/1984 | Gardner, Jr. et al. . |
| 4,538,034 | 8/1985 | French . |
| 4,546,215 | 10/1985 | Ferraro . |
| 4,944,361 | 7/1990 | Lindgren et al. . |
| 5,035,005 | 7/1991 | Hung ........................... 2/209 |
| 5,056,161 | 10/1991 | Breen . |
| 5,068,923 | 12/1991 | Sjöqvist . |

*Primary Examiner*—Diana Biefeld
*Attorney, Agent, or Firm*—Hedman, Gibson & Costigan, P.C.

[57] ABSTRACT

A designer ear muff is disclosed which has (a) a material covered arcuate top section having two ends. The arcuate top section is sized to fit over the top of the head of the wearer and extending downwardly to the wearer's ears where it is attached at each end to a detachable ear covering piece which is removably affixed to each end of the material covered arcuate top section.

2 Claims, 4 Drawing Sheets

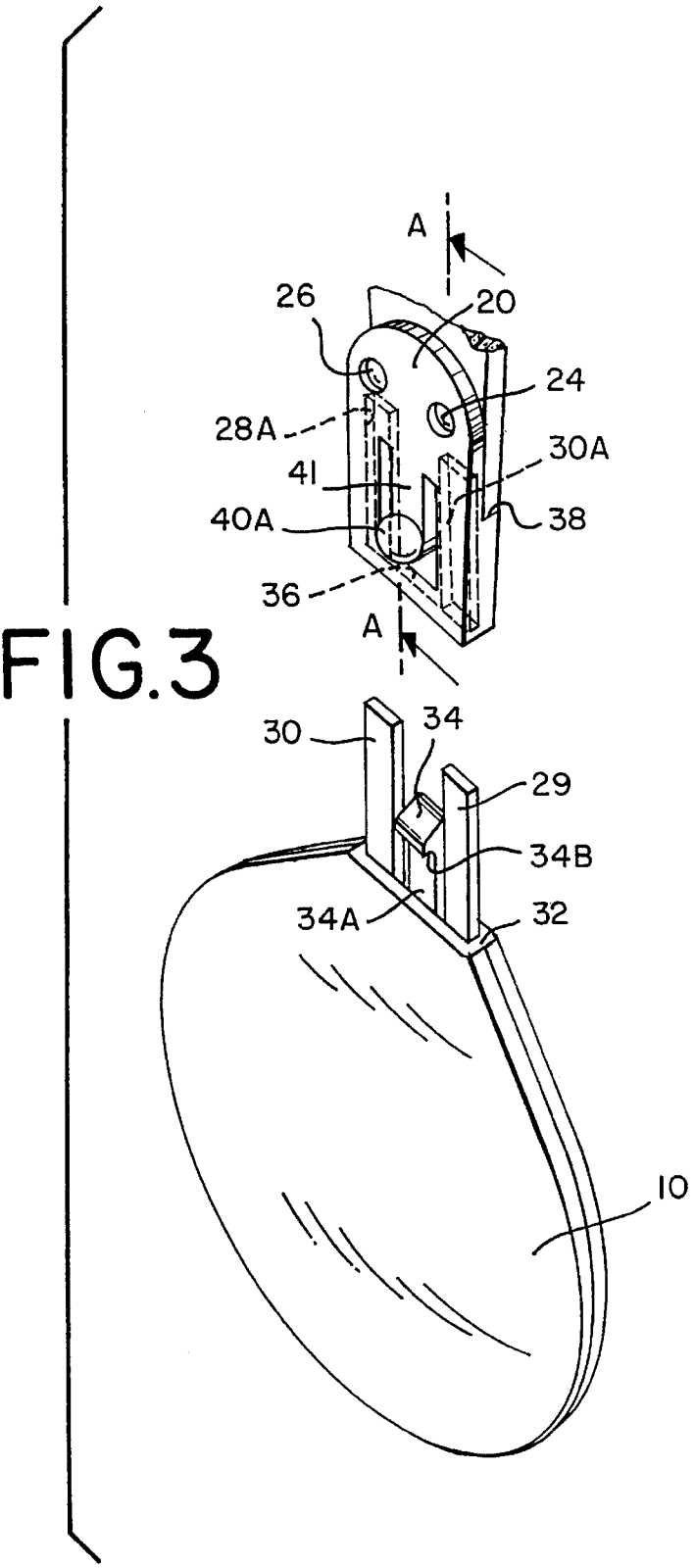

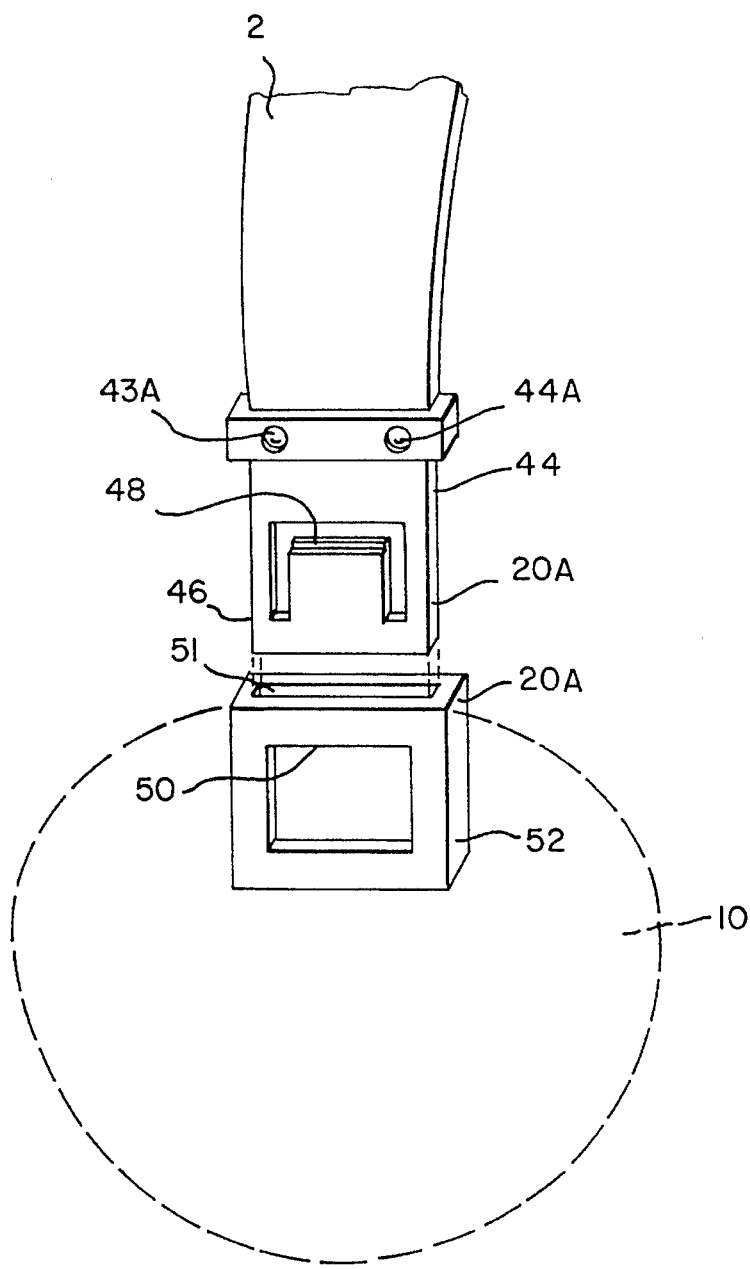
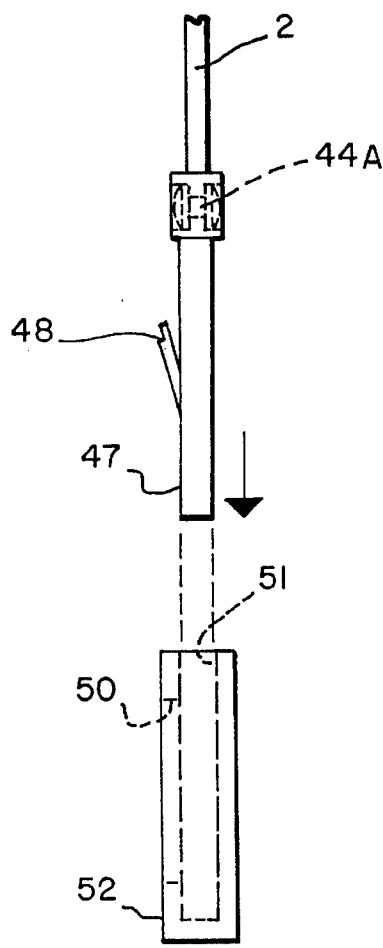
FIG. 6
FIG. 5

DESIGNER EARMUFF HAVING INTERCHANGEABLE EAR MUFF PIECES

BACKGROUND OF THE INVENTION

Earmuffs have long been used to protect the ears during periods of extremely cold weather. These ear muffs have typically been made with a flexible metal curved center section which extends over the head of the wearer and has at each end, a padded ear muff piece that is permanently affixed to be in register with the ear of the wearer.

In addition devices also known as ear muffs have been used to provide acoustic protection to the ear of a wearer against excessive noise such as the sound of a firearm which is discharged or the sound of a jet engine. Devices known as "headsets" or earphones have been used to provide a means for positioning a speaker adjacent to the ear of the user while excluding background noise in order to facilitate the reception of sound.

The prior art devices have been made for explicit utilitarian purposes and have not been made with interchangeable ear pieces that may be changed only for aesthetic purposes.

SUMMARY OF THE INVENTION

The present invention provides a designer ear muff having:

(a) a material covered arcuate top section having a first end and a second end, said arcuate top section being sized to fit over the top of the head of the wearer and extending downwardly to the area of the head which is above each ear of the wearer's ears;

(b) a first detachable ear covering piece which is removably affixed to the first end of said material covered arcuate top section; and (c) a second detachable ear covering piece which is removably affixed to the second end of said material covered arcuate top section.

BRIEF DESCRIPTION OF THE DRAWINGS

FIG. 3 is a detailed drawing of a preferred joint for attaching the ear covering piece to the arcuate top section.

FIG. 4 is a partial section of the upper part of the joint shown in FIG. 3.

FIG. 5 is a side view of the joint of FIG. 6

FIG.6 is a perspective view of an alternative type of joint.

DETAILED DESCRIPTION OF THE INVENTION

The designer ear muff of the invention is based on the use of a material covered arcuate top section which is made of a resilient material that is sized to fit the contour of the head of the wearer with sufficient tension so that the ear muff is retained on the head without placing excessive pressure on the ear lobes.

The ear covering pieces are detachable in order to permit the use of ear covering pieces which have different materials that may be used to color coordinate or accent different items of apparel or fashion accessories such as coats, scarves, dresses, jewelry, handbags and the like or for creating a distinctive appearance for social events. The ear covering piece in FIG. 1 is generally rounded but almost any shape may be utilized such as oval, multi-pointed such as a star, square, triangular or the like may be used.

Generally, it will be preferred to use a material for covering the arcuate top section which will not clash with a wide variety of materials which can be used for the covering of the ear pieces.

Figure 1:
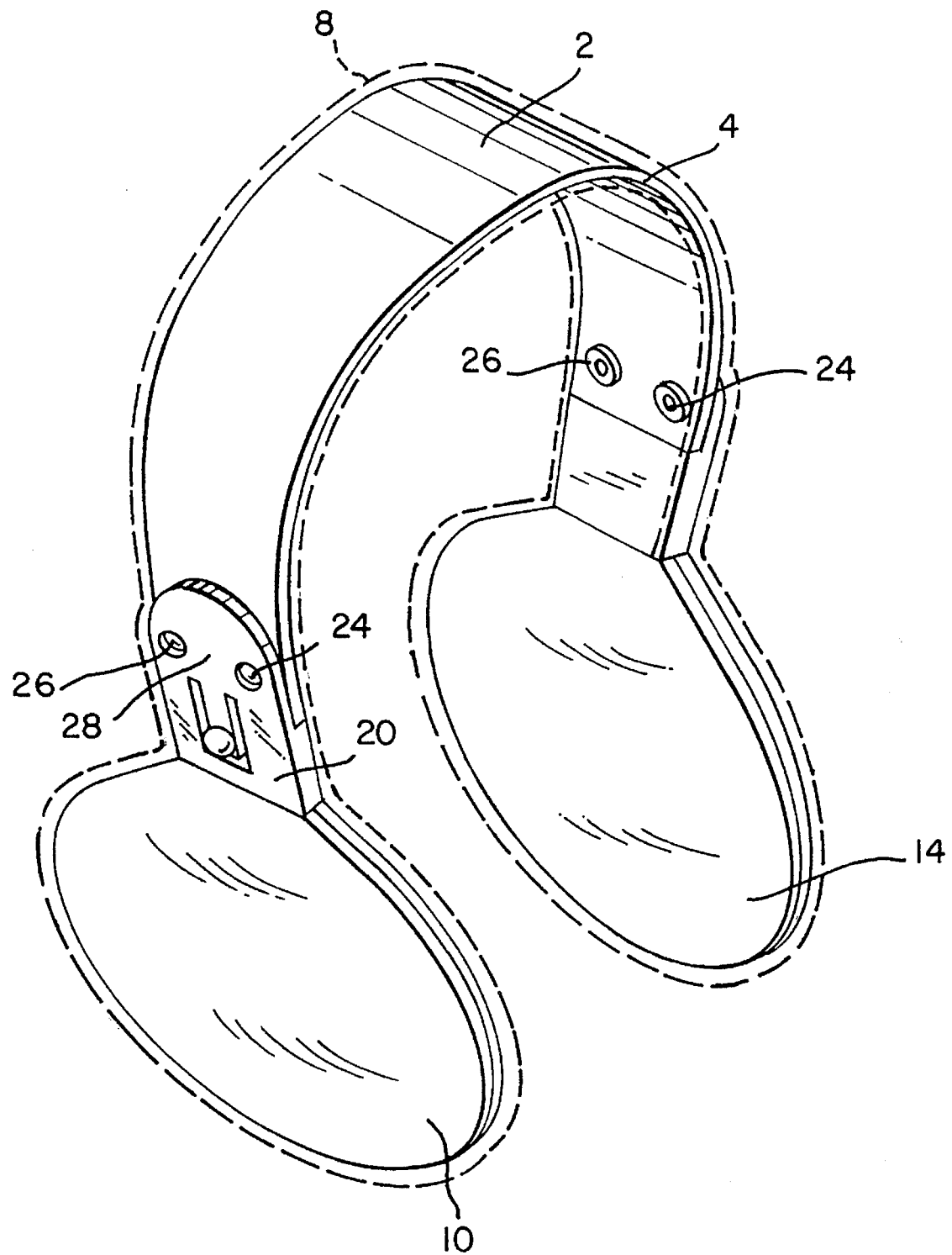
FIG. 1 is a perspective view from the top, front and one side of a designer ear muff of the invention.
Figure 2:
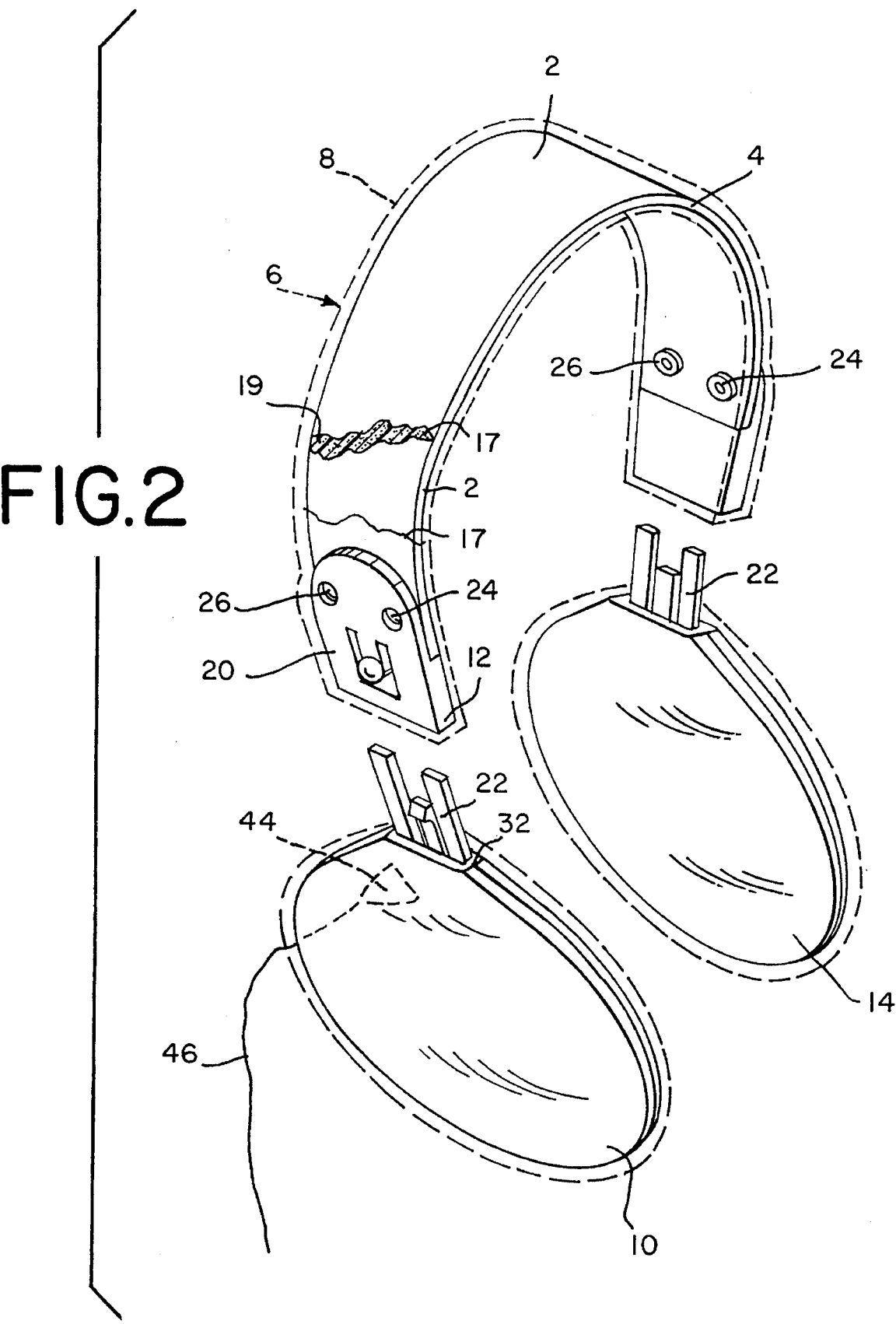
FIG. 2 is an exploded perspective view of the designer ear muff of the invention which shows the ear pieces removed and the attaching means of the ear muff pieces exposed.

As best shown in FIG. 1, the material covered arcuate top section 2 is formed by covering a resilient base element 4 with a material 6 which is shown for purposes of clarity by dotted lines 8. The material may be any suitable woven or non-woven fabric, leather, fur, plastic or the like material. If desired the material may be textured or decorated with precious or semi-precious stones, beads, metallic shapes that sparkle and the like (not shown).It is usually preferred to provide a cushioning layer 19, as shown in FIG. 2, between base element 4 and material layer 6 which will provide a cushioned surface that is placed against the head of the wearer and will provide a puffed or bouffant appearance to arcuate top section 2. The cushioned surface may be provided by any suitable material such as felt, cotton batting, foamed rubber or polyurethane foam.

The arcuate top section may be made with a constant cross-sectional area, with an undulating profile or as shown in FIG. 1 with an upper middle section which is wider than the ends which are tapered ends where they are to be attached to the ear covering pieces.

Cutaway section 17 in FIG. 2 shows the exposed base member 2 which is relatively thin and has a side profile 20. The intermediate polyurethane foam cushioning layer 19 is best seen in FIG. 2. The base member 18 may be made of resilient materials such as plastic, steel, aluminum or the like.

In a preferred embodiment the first detachable ear covering piece 10 is attached to arcuate top section 2 at joint 12 and the second detachable ear covering piece 14 is attached to arcuate top section 2 at joint 16. The ear covering pieces have attachment means 22 which interlock with joint 20 on the arcuate top section 2. The Joint 20 is riveted onto the arcuate top section 2 by rivets 24 and 26 which are placed in holes that are drilled in both the arcuate top section 2 and in the joint 20. It is preferred to recess the holes on the outer facing surface 28 of joint element 20 in order to provide a completely smooth surface which is covered by the material 8.

The preferred attachment means are shown in FIG. 3. Although any suitable snap, hook and eye, magnetic or other mechanical connection may be used, a three component, rectangular post and sleeve connector is preferred. The upper part 32 of the ear covering piece may be provided with a fastener having two elongated end posts 28 and 30 which have rectangular cross-sections. These posts are sized to fit within sleeves 28A and 30A in joint element 20 to act as stabilizer bars to prevent any rotational movement between the arcuate top section 2 and the ear covering piece 10. The upper end 34 of center post 34A has a retaining catch 34B which secures center post 34A within sleeve 36 in joint element 20. Center post 34A preferably has a rectangular cross-section to prevent rotation of the ear covering piece relative to the arcuate top section. The joint element 20 is also provided with an shelf edge 38 which acts as a receiving stop for arcuate top section 2.

A cross-section, of the connected joint element 20 and upper part 32 of the ear covering piece, through the line A—A of FIG. 3 is shown in FIG. 4. The upper end 34 of center post 34A is shown in sleeve 36 with retaining catch 34B in contact with latch point 40. The latch point 40 is affixed to post 42. The latch is opened by pushing button 40A which is mounted on movable post 44. The latch is released when internal button 40B is pushed inwardly to contact and deflect upper end 34 of center post 34A.

As best seen in FIG. 6, the alternative joint 20A comprises a male and female part which lock together. The upper part 44 has a frame section 46 which has a movable latch 48 that engages shoulder 50 when it is inserted into pocket 51 of lower part 52. The upper part is mounted to the arcuate top section by rivets 43A and 44A through holes (not shown). The lower part 52 serves as a mounting means for the ear muff 10 which is shown by the dotted lines.

The latch 48 is shown in FIG. 5 in a side view. The latch 42 is mounted one flexible post 47 which is an integral living hinge that is molded into upper part 44. The pocket 51 is shown by dotted lines in lower part 52 in FIG.5. The shoulder 50 is also shown by dotted lines in FIG. 5. The latch 48 has a recessed edge which engages the edge of shoulder 50. Both joints may be may of a resilient plastic such as polystyrene or other suitable molding resin.

While the invention as shown in the drawings is illustrated as an item of apparel, it is intended that the ear covering piece may be made with an associated wired or wireless earphone which would enable the interchangeable ear muffs to function in combination with an electronic apparatus such as a radio receiver, tape player, CD player or the like. FIG. 2 shows an embedded speaker 44 with associated connecting wire 46 which is connected to an electronic apparatus (not shown).

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. A designer ear muff which consists essentially of:
(a) a fabric covered arcuate top section having a first end and a second end, said arcuate top section being sized to fit over the top of the head of a wearer and extending downwardly to the area of the head which is above each of a wearer's ears;
(b) a first detachable, material covered ear covering piece which is removably affixed to the first end of said fabric covered arcuate top section, wherein said fabric covered arcuate top section is provided with an intermediate cushioning layer; and
(c) a second detachable material covered ear covering piece which is removably affixed to the second end of said material covered arcuate top section said fabric covered arcuate top section having a widened middle section and having said first end and said second end tapered at the point where they are adapted to be attached to said first detachable material covered ear covering piece and said second detachable material covered ear covering piece.

2. A designer ear muff which consists essentially of:
(a) a fabric covered arcuate top section having a first end and a second end, said arcuate top section having a continuous arc and being sized to fit over the top of the head of a wearer and extending downwardly to the area of the head which is above each of a wearer's ears;
(b) a first detachable material covered ear covering piece which is removably affixed to the first end of said fabric covered arcuate top section; and
(c) a second detachable material covered ear covering piece which is removably affixed to the second end of said fabric covered arcuate top section said fabric covered arcuate top section having a widened middle section and having said first end and said second end tapered at the point where they are adapted to be attached to said first detachable material covered ear covering piece and said second detachable material covered ear covering piece, said first detachable material covered ear covering piece and said second detachable material covered ear covering piece being attached to said arcuate top section by a joint which comprises a male and female part which lock together, said male part having a frame section with a movable latch that engages a shoulder in a pocket in said female part.

* * * * *